(12) United States Patent
Kim et al.

(10) Patent No.: US 9,532,726 B2
(45) Date of Patent: Jan. 3, 2017

(54) IMPLANTABLE WIRELESS ELECTROCARDIOGRAM SENSOR DEVICE

(71) Applicant: INDUSTRY ACADEMIC COOPERATION FOUNDATION, KEIMYUNG UNIVERSITY, Daegu (KR)

(72) Inventors: Yoon Nyun Kim, Daegu (KR); Jong Ha Lee, Seoul (KR); Hee Jun Park, Daegu (KR); Hyoung Seob Park, Daegu (KR); Chang Sik Son, Daegu (KR)

(73) Assignee: INDUSTRY ACADEMIC COOPERATION FOUNDATION KEIMYUNG UNIVERSITY, Dalseo-Gu, Daegu (KR)

( * ) Notice: Subject to any disclaimer, the term of this patent is extended or adjusted under 35 U.S.C. 154(b) by 0 days.

(21) Appl. No.: 14/764,983

(22) PCT Filed: Jan. 27, 2014

(86) PCT No.: PCT/KR2014/000757
§ 371 (c)(1),
(2) Date: Jul. 31, 2015

(87) PCT Pub. No.: WO2014/119890
PCT Pub. Date: Aug. 7, 2014

(65) Prior Publication Data
US 2015/0374253 A1      Dec. 31, 2015

(30) Foreign Application Priority Data

Jan. 31, 2013   (KR) .................. 10-2013-0011250

(51) Int. Cl.
*A61B 5/042*       (2006.01)
*A61B 5/0402*     (2006.01)
(Continued)

(52) U.S. Cl.
CPC ........... *A61B 5/0422* (2013.01); *A61B 5/0006* (2013.01); *A61B 5/0031* (2013.01); *A61B 5/0402* (2013.01);
(Continued)

(58) Field of Classification Search
CPC ................ A61B 5/6861; A61B 5/0422; A61B 2560/0406; A61B 2560/0418; A61N 1/37205; A61N 1/37229; A61N 1/3756; A61N 1/375
See application file for complete search history.

(56) References Cited

U.S. PATENT DOCUMENTS

2005/0027204 A1   2/2005   Kligfield et al.
2005/0245971 A1   11/2005  Brockway et al.
(Continued)

FOREIGN PATENT DOCUMENTS

KR   10-2002-0089669 A   11/2002
KR   10-2012-0081583 A   7/2012
(Continued)

OTHER PUBLICATIONS

International Search Report for PCT/KR2014/000757 mailed May 26, 2014 from Korean Intellectual Property Office.

*Primary Examiner* — Michael Kahelin
(74) *Attorney, Agent, or Firm* — Revolution IP, PLLC

(57) ABSTRACT

Disclosed is an implantable wireless electrocardiogram sensor device, including: a cylindrical capsule provided with four recesses on a lateral surface thereof in a longitudinal direction thereof at equal intervals; electrodes installed on upper and lower surfaces of the cylindrical capsule and configured to measure electrocardiogram; a wireless electrocardiogram sensor module installed inside the capsule; a data transceiving antenna wound around two recesses symmetrical at a center; and a coil for charging wound around
(Continued)

the remaining two recesses in a direction vertical to the antenna.

11 Claims, 3 Drawing Sheets

(51) Int. Cl.
*A61B 5/00* (2006.01)
*H02J 5/00* (2016.01)
*H02J 7/02* (2016.01)

(52) U.S. Cl.
CPC .............. *A61B 5/042* (2013.01); *A61B 5/686* (2013.01); *A61B 5/6861* (2013.01); *H02J 5/005* (2013.01); *H02J 7/025* (2013.01); *A61B 2560/0219* (2013.01)

(56) References Cited

U.S. PATENT DOCUMENTS

| | | | |
|---|---|---|---|
| 2008/0284599 | A1 | 11/2008 | Zdeblick et al. |
| 2013/0274567 | A1 | 10/2013 | Grosser et al. |

FOREIGN PATENT DOCUMENTS

| | | | |
|---|---|---|---|
| WO | 2007-028035 | A2 | 3/2007 |
| WO | 2012-048907 | A1 | 4/2012 |

(a)

(b)

IMPLANTABLE WIRELESS ELECTROCARDIOGRAM SENSOR DEVICE

CROSS REFERENCE TO PRIOR APPLICATIONS

This application is a National Stage Application of PCT International Patent Application No. PCT/KR2014/000757 filed on Jan. 27, 2014, under 35 U.S.C. §371, which claims priority to Korean Patent Application No. 10-2013-0011250 filed on Jan. 31, 2013, which are all hereby incorporated by reference in their entirety.

TECHNICAL FIELD

The present invention relates to an implantable electrocardiogram sensor, and more particularly, to an implantable wireless electrocardiogram sensor device, which is easily implantable into a part of a body, and capable of continuously measuring and efficiently monitoring electrocardiogram.

BACKGROUND ART

An electrocardiogram records a change in a voltage by installing a sensor on a skin around a heart. The voltage measured by the sensor installed on the skin has an analog characteristic. A general method of measuring an electrocardiogram is a method of measuring a change in a voltage by using a potential difference measuring method to measure a fine voltage.

However, when it is necessary to enlarge an electrocardiogram graph in order to obtain fine information, most of the electrocardiogram measuring equipment in the related art directly increases a potential difference to obtain a more precise result. However, it is impossible to unlimitedly increase a potential difference, and when a potential difference is increased, a phenomenon, in which a current reversely flows, may occur due to a potential difference with a body.

Further, existing electrocardiogram equipment is configured so that one equipment uses the predetermined number of leads. However, when a predetermined lead is not attached onto a body for each equipment, there is a problem in that it is impossible to read a measured electrocardiogram signal or obtain necessary information.

Further, the existing electrocardiogram equipment adopts a fixed unit recording method according to a time order, so that it is very inconvenient to variously make a search according to a situation. Accordingly, in order to search for stored material in electrocardiogram equipment capable of storing materials, it is necessary to inconveniently search for the material according to a recorded order.

In order to solve the problem, an implantable electrocardiogram sensor, which is directly transplanted or implanted into a human body to more accurately measure a signal, has been developed, but the implantable electrocardiogram sensor needs to continuously transmit a signal for 24 hours, so that there is a problem in that a capacity of a power supply needs to be large, and when a large capacity battery is used in order to solve the problem, the implantable electrocardiogram sensor has a large size, so that an extensive surgical operation needs to be performed in order to implant the implantable electrocardiogram sensor into the human body.

DISCLOSURE

Technical Problem

In order to solve the aforementioned problems, an object of the present invention is to provide an implantable wireless electrocardiogram sensor device, which is wirelessly chargeable even at a remote distance, has a small size enough to be implantable into a human body by simply cutting only a local region of the human body, and is capable of continuously measuring and monitoring electrocardiogram data for a long time.

Technical Solution

In order to solve the aforementioned objects, an exemplary embodiment the present invention provides an implantable wireless electrocardiogram sensor device, including: a cylindrical capsule provided with four recesses on a lateral surface thereof in a longitudinal direction thereof at equal intervals; electrodes installed on upper and lower surfaces of the cylindrical capsule and configured to measure electrocardiogram; a wireless electrocardiogram sensor module installed inside the capsule; a data transceiving antenna wound around two recesses symmetrical at a center; and a coil for charging wound around the remaining two recesses in a direction vertical to the antenna.

The wireless electrocardiogram sensor module may include: a wireless power receiving module configured to receive power induced through the coil for charging; a chargeable battery module charged with the received power; an electrocardiogram data processing module configured to process electrocardiogram data input through the electrodes; an electrocardiogram data transceiving module configured to wirelessly transceive the electrocardiogram data with an external device; and a main controller configured to collectively control the wireless electrocardiogram sensor module.

Further, an electrode may be installed at a center of a lateral surface of the cylindrical capsule, and electrocardiogram may be measured with the three electrodes together with the electrodes installed on the upper and lower surfaces of the cylindrical capsule, and the wireless electrocardiogram sensor module may further include an auxiliary battery for supplying emergency power.

The capsule may be a quadrangular cylindrical form, the four recesses may be formed at corners of the quadrangular cylindrical capsule, the electrocardiogram data transceiving module may include a Bluetooth or ZigBee device, and the coil for charging may use a frequency resonance coil.

Advantageous Effects

The implantable wireless electrocardiogram sensor device according to the present invention has the form implanted into a part of a heart or a human body for measuring electrocardiogram, includes the constituent elements for wireless charging in order to continuously transmit a signal for 24 hours, and is configured so that a length of the coil is sufficiently secured so as to perform wireless charging even at a remote distance and the antenna for transceiving is also installed to be wound around the capsule, and has the structure, in which the coil for wireless charging and the antenna for transceiving are wound around the electrocardiogram sensor device in the form of the small implantable capsule while crossing each other, so that it is possible to easily implant the implantable wireless electrocardiogram sensor device into a measurement region of the human body, measure and monitor electrocardiogram for a long time, and efficiently transceive wireless electrocardiogram data.

BEST MODE

Figure 1:
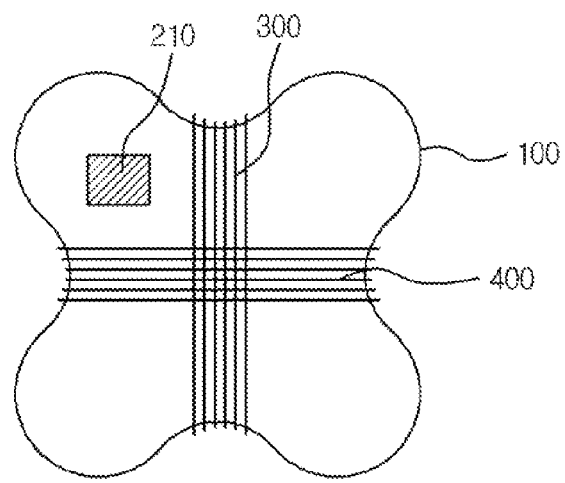
FIG. 1 is a front view and a side view of an implantable wireless electrocardiogram sensor device according to an exemplary embodiment of the present invention.
Figure 1:
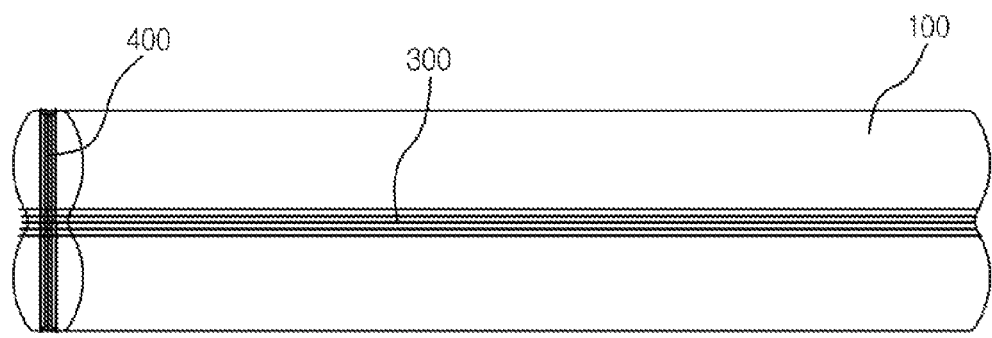

FIGS. 1A and 1B are a front view and a side view of an implantable wireless electrocardiogram sensor device according to an exemplary embodiment of the present invention. As illustrated in FIG. 1, the implantable wireless electrocardiogram sensor device according to the exemplary embodiment of the present invention includes: a cylindrical capsule 100 provided with four recesses on a lateral surface thereof in a longitudinal direction thereof at equal intervals; measuring electrodes 210 installed on an upper surface and a lower surface of the cylindrical capsule 100 and measuring electrocardiogram; a wireless electrocardiogram sensor module 200 installed inside the capsule 100; a data transceiving antenna 300 wound around two recesses which are symmetrical at a center; and a coil 400 for charging wound around the remaining two recesses in a vertical direction to the data transceiving antenna.

As described above, the present invention suggests a structure, in which the antenna and the coil for wirelessly charging power are wound around an external surface of the cylindrical capsule 100 to be vertical to each other in a longitudinal direction, as the implantable wireless electrocardiogram sensor device, and suggests a sensor device, which has a form of the capsule 100 capable of being simply implantable into a human body by cutting a skin by several centimeters without a transplant through an extensive surgical operation, and in which the coil 400 for charging for wirelessly charging a battery is installed in order to measure and monitor electrocardiogram for 24 hours, and the coil 400 for charging is installed to be vertical to the antenna, thereby decreasing an interference effect and efficiently and wirelessly charging the battery and transceiving data.

MODE FOR CARRYING OUT THE INVENTION

Advantages and features of the present invention and methods for accomplishing the same will be described through the exemplary embodiments described in detail below together with the accompanying drawings. However, the present invention is not limited to the exemplary embodiments described herein, and may be implemented in other forms. However, the present exemplary embodiments are provided for describing the present invention in detail so that those skilled in the art may easily carry out the technical spirit of the present invention.

In the drawings, the exemplary embodiments of the present invention are not limited to the illustrated specific forms, but are exaggerated for the purpose of clarity. In addition, like reference numerals designate like elements throughout the specification.

In the present specification, the term "and/or" is understood to include at least one of the constituent elements that are enumerated in the context. In addition, a singular form also includes a plural form unless particularly stated. Further, a constituent element, a step, an operation, and a device mentioned with "include" or "including" used in the specification means existence or addition of one or more other constructional elements, steps, operations, and elements, and devices.

Hereinafter, an exemplary embodiment of to the present invention will be described in detail with reference to the drawings.

FIGS. 1A and 1B are a front view and a side view of an implantable wireless electrocardiogram sensor device according to an exemplary embodiment of the present invention. As illustrated in FIG. 1, the implantable wireless electrocardiogram sensor device according to the exemplary embodiment of the present invention includes: a cylindrical capsule 100 provided with four recesses on a lateral surface thereof in a longitudinal direction thereof at equal intervals; measuring electrodes 210 installed on an upper surface and a lower surface of the cylindrical capsule 100 and measuring electrocardiogram; a wireless electrocardiogram sensor module 200 installed inside the capsule 100; a data transceiving antenna 300 wound around two recesses which are symmetrical at a center; and a coil 400 for charging wound around the remaining two recesses in a vertical direction to the data transceiving antenna.

As described above, the present invention suggests a structure, in which the antenna and the coil for wirelessly charging power are wound around an external surface of the cylindrical capsule 100 to be vertical to each other, as the implantable wireless electrocardiogram sensor device, and suggests a sensor device, which has a form of the capsule 100 capable of being simply implantable into a human body by cutting a skin by several centimeters without requiring a transplant through a big surgical operation, and in which the coil 400 for charging for wirelessly charging a battery is installed in order to measure and monitor electrocardiogram for 24 hours, and the coil 400 for charging is installed to be vertical to the antenna, thereby decreasing an interference effect and efficiently and wirelessly charging the battery and transceiving data.

Here, the cylindrical capsule 100 serving as a housing has a structure, in which an internal side thereof is hollow, the wireless electrocardiogram sensor module 200 capable of measuring electrocardiogram is inserted into and mounted in the cylindrical capsule 100, and the electrodes 210 capable of measuring the electrocardiogram are installed on the upper surface and the lower surface of the cylindrical capsule 100.

The cylindrical capsule 100 may have a completely sealed structure for waterproofing an internal circuit board, and be formed of an insulating material, such as plastic. Further, the cylindrical capsule 100 has a structure, in which the four recesses are formed on the lateral surface thereof in the longitudinal direction thereof at the equal intervals, so that one electrocardiogram data transceiving antenna 300 passing through a center axis and the coil 400 for charging for wirelessly charging power are vertically wound.

As described above, the antenna and the coil 400 for charging need to secure sufficient lengths in the small cylindrical capsule 100, so that the antenna and the coil 400 for charging are formed to be wound around the external surface of the cylindrical capsule 100 in the longitudinal direction of the cylindrical capsule 100, thereby maximally securing lengths. Further, it is suggested that the cylindrical capsule 100 is provided with the recesses on the lateral surface thereof in the longitudinal direction thereof at the equal intervals so that the antenna and the coil 400 for charging may easily and certainly wound.

Further, the antenna and the coil 400 for charging have the structure, in which the antenna and the coil 400 for charging are wound while vertically crossing each other, so that an interference effect incurable in the antenna for transceiving data and the coil receiving power for charging may be maximally reduced, thereby stably and efficiently transceiving data and charging power.

The implantable electrocardiogram sensor is implanted into the skin by cutting a part (about 3 cm) of a skin of a heart region and wirelessly used, so that the implantable electrocardiogram sensor requires power for operation for 24 hours or more. However, in the related art, the electrocardiogram sensor may be a device attached onto a skin in a patch type to monitor electrocardiogram by connecting a lead of the electrode 210 through a wire, or when the electrocardiogram sensor is a wireless type, there is a problem in that it is not easy to monitor electrocardiogram for 24 hours or more with power of the battery used.

In this respect, the present invention suggests the implantable wireless electrocardiogram sensor device, in which the coil 400 for wireless charging is wound around the external side of the cylindrical capsule 100 in the longitudinal direction thereof, and the antenna for data transceiving is wound to be vertical to the coil 400 again, thereby stably transceiving data and wirelessly charging the battery without mutual interference.

Figure 2:
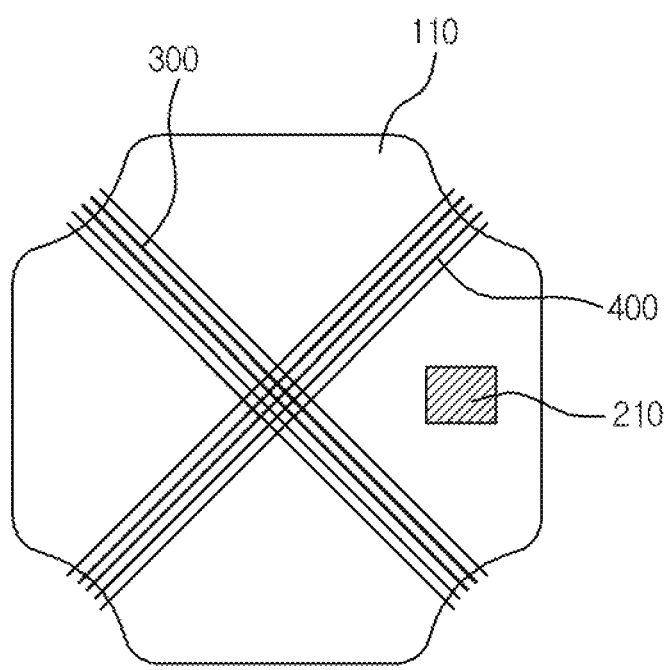
FIG. 2 is a front view of an implantable wireless electrocardiogram sensor device according to another exemplary embodiment of the present invention.

FIG. 2 is a front view of an implantable wireless electrocardiogram sensor device according to another exemplary embodiment of the present invention. Unlike the exemplary embodiment of FIG. 1, the exemplary embodiment illustrated in FIG. 2 is a structure, in which a capsule 100 has a quadrangular cylindrical form and four recesses are formed at corners of the quadrangular cylindrical capsule 100, so that an antenna 300 for transceiving electrocardiogram data and a coil 400 for charging are wound around the quadrangular cylindrical capsule 100.

The exemplary embodiment illustrated in FIG. 2 suggests the structure, in which the capsule 100 has the quadrangular cylindrical form and the recesses are formed at the four corners of the quadrangular cylindrical capsule 100, so that the antenna 300 for transceiving electrocardiogram data and the coil 400 for charging are wound around the quadrangular cylindrical capsule 100 in a longitudinal direction thereof while crossing each other, thereby securing larger lengths of the antenna and the coil 400 for charging on the same volume.

Figure 3:
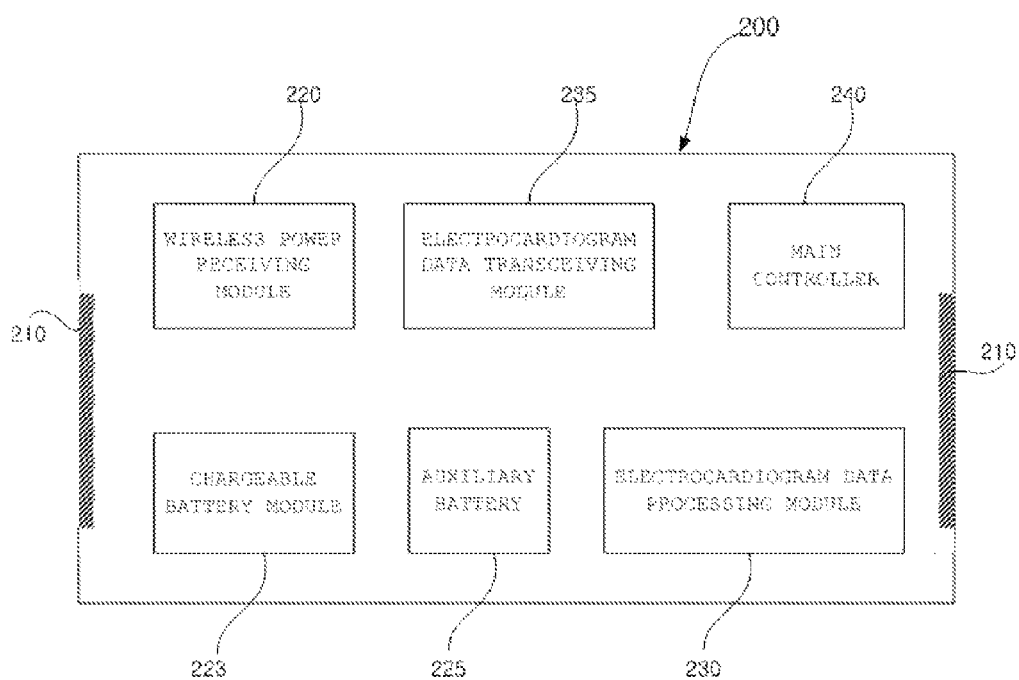
FIG. 3 is a diagram illustrating a block configuration of a wireless electrocardiogram sensor module in the implantable wireless electrocardiogram sensor device according to the exemplary embodiment of the present invention.

FIG. 3 is a diagram illustrating a block configuration of a wireless electrocardiogram sensor module 200 in the implantable wireless electrocardiogram sensor device according to the exemplary embodiment of the present invention. As illustrated in FIG. 3, the wireless electrocardiogram sensor module 200 includes a wireless power receiving module 220 receiving induced power through the coil 400 for charging, a chargeable battery module 223 charged with the received power, an electrocardiogram data processing module 230 processing electrocardiogram data input through the electrode 210, an electrocardiogram data transceiving module 235 wirelessly transceiving the electrocardiogram data with an external device, and a main controller 240 collectively controlling the wireless electrocardiogram sensor module 200.

That is, a measured potential signal corresponding to a fine potential measured through the leads of the electrodes 210 installed on the upper and lower surfaces of the capsule 100 inserted into a peripheral region of the heart is generated, and the sensor module 200 performs a function of detecting a change in a fine potential generated inside the skin around the heart.

A condenser, a voltage measuring device, a reference potential generating unit, an A/D converter, and the like (not illustrated) are provided as the electrocardiogram data processing module 230 between both electrodes 210 installed on the upper and lower surfaces of the capsule 100, and the condenser stabilizes the measured potential signal input from the measuring electrodes 210. That is, the condenser stabilizes the measured potential signal so that the a potential is measured within an error range of 0.001% or lower in order to adjust the measured potential and accurately output a result about a difference between the measured potential and the reference potential, and further performs a function of correcting a change in a potential generated by an impact or a change of a surrounding environment (static electricity and a magnetic field).

The voltage measuring device is connected with the condenser and the reference potential generating unit, and compares the stabilized measured potential signal with the reference potential of the reference potential generating unit and generates a measured potential signal that is a difference between the measured potential and the reference potential.

The reference potential generating unit is connected with the condenser and the voltage measuring device, and measures a fine potential by using power supplied from the battery module for charging or an auxiliary battery and generates the reference potential actually necessary for generating a potential to apply the generated reference potential to the condenser and the voltage measuring device, respectively. Further, the A/D converter 130 converts the measured potential signal that is an analog signal input through the electrodes 210 into actual potential data that is a digital signal and outputs the actual potential data. Here, the actual potential data is a quantized value of the measured potential signal.

Further, the electrocardiogram data processed by the electrocardiogram data processing module 230 is transmitted to an external terminal through the electrocardiogram data transceiving module 235. The electrocardiogram data transceiving module 235 is a near field wireless communication device, and may use a Bluetooth or ZigBee device.

As exemplified in FIGS. 1 and 2, in the exemplary embodiment of the present invention, the electrocardiogram of a patient needs to be continuously monitored for 24 hours or more, so that in order to solve insufficient power of a single-use battery mounted in the wireless electrocardiogram sensor module 200, power is wirelessly received through the coil 400 for charging wound around the external surface of the capsule and power is continuously charged with the received power through the chargeable battery module 223.

General wireless charging technology is technology for making a current flow to a coil of a wireless charging device and wirelessly applying electromagnetic waves generated in the coil to the coil 400 for charging to induce power. The technology is divided into a magnetic resonance scheme and a magnetic induction scheme, and the magnetic resonance scheme is a scheme of creating an equal electromagnetic field (resonance) and charging power by mounting resonant coils having the same frequency in a transmitting unit and a receiving unit, and may charge power at a remote distance of several meters. The electromagnetic induction scheme is a scheme, in which a current flows through electromagnetic induction and then a magnetic field generated in a first coil of a transmitting unit is induced to a secondary coil of a receiving unit to supply the current, and the transmitting unit is adjacent to the receiving unit within several centimeters to charge power.

In the exemplary embodiment of the present invention, both two schemes are available, but the coil is wound around the capsule 100 in the longitudinal direction of the capsule 100, so that it is possible to sufficiently secure a length of the coil, and thus the battery may be charged through the resonant coil by using the magnetic resonance scheme. When the aforementioned scheme is used, it is possible to conveniently and wirelessly charge the battery within several meters from a patient without necessity to attach a patch for charging and the like onto a part of the implanted electrocardiogram sensor device.

In addition, as illustrated in FIG. 3, the implantable wireless electrocardiogram sensor device according to the exemplary embodiment of the present invention may further include an auxiliary battery 22 to continuously supply power without interruption of measurement or the monitoring of electrocardiogram when there is a problem in wireless charging.

As described above, the implantable wireless electrocardiogram sensor device according to the exemplary embodiment of the present invention has the form implanted into a part of a heart or a human body for measuring electrocardiogram, includes the constituent elements for wireless charging in order to continuously transmit a signal for 24 hours, and is configured so that a length of the coil is sufficiently secured so as to perform wireless charging even at a remote distance and the antenna for transceiving is also installed to be wound around the capsule 100, and has the structure, in which the coil 400 for wireless charging and the antenna 300 for transceiving are wound around the electrocardiogram sensor device in the form of the small implantable capsule 100 while crossing each other, so that it is possible to easily implant the implantable wireless electrocardiogram sensor device into a measurement region of the human body, measure and monitor electrocardiogram for a long time, and efficiently transceive wireless electrocardiogram data.

In the above description, the present invention has been illustrated and described in relation to the specific exemplary embodiment, but those skilled in the art may easily recognize that various modifications and changes can be made without departing from the spirit and the region of the invention according to the claims.

INDUSTRIAL APPLICABILITY

The present invention relates to an implantable electrocardiogram sensor, and more particularly, to an implantable wireless electrocardiogram sensor device, which is easily implantable into a part of a body, and capable of continuously measuring and efficiently monitoring electrocardiogram, thereby being industrially applicable.

The invention claimed is:

1. An implantable wireless electrocardiogram sensor device, comprising:
   a cylindrical capsule provided with four recesses on a lateral surface thereof in a longitudinal direction thereof at equal intervals;
   electrodes installed on upper and lower surfaces of the cylindrical capsule and configured to measure electrocardiogram;
   a wireless electrocardiogram sensor module installed inside the capsule;
   a data transceiving antenna wound around two recesses symmetrical at a center; and
   a coil for charging wound around the remaining two recesses in a direction vertical to the antenna.

2. The implantable wireless electrocardiogram sensor device of claim 1, wherein the wireless electrocardiogram sensor module includes:
   a wireless power receiving module configured to receive power induced through the coil for charging;
   a chargeable battery module charged with the received power;
   an electrocardiogram data processing module configured to process electrocardiogram data input through the electrodes;
   an electrocardiogram data transceiving module configured to wirelessly transceive the electrocardiogram data with an external device; and
   a main controller configured to collectively control the wireless electrocardiogram sensor module.

3. The implantable wireless electrocardiogram sensor device of claim 1, wherein an electrode is installed at a center of a lateral surface of the cylindrical capsule, and electrocardiogram is measured with the three electrodes together with the electrodes installed on the upper and lower surfaces of the cylindrical capsule.

4. The implantable wireless electrocardiogram sensor device of claim 1, wherein the wireless electrocardiogram sensor module further includes an auxiliary battery for supplying emergency power.

5. The implantable wireless electrocardiogram sensor device of claim 1, wherein the capsule is a quadrangular cylindrical form, and the four recesses are formed at corners of the quadrangular cylindrical capsule.

6. The implantable wireless electrocardiogram sensor device of claim 2, wherein the electrocardiogram data transceiving module includes a Bluetooth or ZigBee device.

7. The implantable wireless electrocardiogram sensor device of claim 1, wherein the coil for charging uses a frequency resonance coil.

8. The implantable wireless electrocardiogram sensor device of claim 2, wherein an electrode is installed at a center of a lateral surface of the cylindrical capsule, and electrocardiogram is measured with the three electrodes together with the electrodes installed on the upper and lower surfaces of the cylindrical capsule.

9. The implantable wireless electrocardiogram sensor device of claim 2, wherein the wireless electrocardiogram sensor module further includes an auxiliary battery for supplying emergency power.

10. The implantable wireless electrocardiogram sensor device of claim 2, wherein the capsule is a quadrangular cylindrical form, and the four recesses are formed at corners of the quadrangular cylindrical capsule.

11. The implantable wireless electrocardiogram sensor device of claim 2, wherein the coil for charging uses a frequency resonance coil.

* * * * *